United States Patent [19]

House et al.

[11] Patent Number: 4,843,884

[45] Date of Patent: Jul. 4, 1989

[54] METHOD AND SYSTEM FOR ULTRASONIC DETECTION OF FLAWS IN TEST OBJECTS

[75] Inventors: Larry J. House, Columbus; James F. Mank, Dublin; Thomas A. Pettenski, Columbus; William J. Williams, Columbus; Donald T. Hayford, Columbus, all of Ohio

[73] Assignee: Gas Research Institute, Chicago, Ill.

[21] Appl. No.: 927,511

[22] Filed: Nov. 6, 1986

[51] Int. Cl.$^4$ .......................................... G01N 29/04
[52] U.S. Cl. ...................................... 73/622; 73/637; 73/644
[58] Field of Search .................. 73/622, 637, 644, 626, 73/627

[56] References Cited

U.S. PATENT DOCUMENTS

| | | | |
|---|---|---|---|
| 3,426,585 | 2/1969 | Zemanek, Jr. et al. | 73/622 |
| 3,921,440 | 11/1975 | Toth | 73/622 |
| 3,955,425 | 5/1976 | Corneau | 73/622 |
| 3,958,451 | 5/1976 | Richardson | 73/644 |
| 3,981,184 | 9/1976 | Matay | 73/622 |
| 4,084,444 | 4/1978 | Lewis | 73/622 |
| 4,328,708 | 5/1982 | Bagwell | 73/622 |
| 4,375,165 | 3/1983 | de Sterke | 73/622 |
| 4,434,660 | 3/1984 | Michaels et al. | 73/622 |
| 4,472,975 | 9/1984 | Beck et al. | 73/622 |
| 4,672,852 | 6/1987 | Gugel et al. | 73/637 |

FOREIGN PATENT DOCUMENTS

| | | | |
|---|---|---|---|
| 2936660 | 3/1981 | Fed. Rep. of Germany | 73/637 |
| 1164456 | 9/1969 | United Kingdom | 73/622 |

OTHER PUBLICATIONS

A. deSterke, "Automatic Ultrasonic Inspection of Pipeline Welds" NDT International, Dec. 1980, vol. 13, No. 6.

Green R., Jr., "Effect of Metallic Microstructure on Ultrasonic Attenuation" Nondestructive Evaluation: Microstructional Characterization and Reliability Stragtegies, O Ho Buck and Stanley M. Wolf, Proceedings of the Metallurgient Soc. of AIME, TMS Fall Meeting Ptg. PA (Oct. 5-9 1980) pp. 115-121.

Hartman B. et al, "Ultrasonic Hysteresis Absorption in Polymers" NOLTR 72-187, Aug. 1972.

Table of Ulfrasonic Properties, Metrotek, Inc. AN 23(10/82).

Hartman B. et al. "Immersion Apparatus for Ultrasonic Measurements" NOLTR 72-73 p. 14 (Apr. 14, 1972).

Primary Examiner—Stewart J. Levy
Assistant Examiner—Laurence G. Fess
Attorney, Agent, or Firm—Watkins, Dunbar & Pollick

[57] ABSTRACT

A method, apparatus and system for the ultrasonic detection and evaluation of flaws in annular test objects including an arrangement of ultrasonic transducers that are rotated about the outer surface of the test object and provide an ultrasonic indication fo flaws in the object, and for electronically collecting, storing, and analyzing the flaw data gathered by the ultrasonic transducers, to further provide a predetermined objective indicia of acceptablility concerning the structural integrity of the test object.

17 Claims, 10 Drawing Sheets

METHOD AND SYSTEM FOR ULTRASONIC DETECTION OF FLAWS IN TEST OBJECTS

FIELD OF THE INVENTION

The invention relates to ultrasonic detection of flaws in test objects, and to electronic analysis of data gathered thereby. More particularly, the invention relates to the detection of flaws at the fusion point between segments in a pipe line, using ultrasonic transducers, and to the complete electronic analysis of the data resulting in a simple print out of an accept or reject statement concerning the fusion point. The invention focuses more specifically on the detection of flaws in butt fused polyethylene pipe joints.

BACKGROUND OF THE INVENTION

Butt fused polyethylene pipe is used extensively by domestic and foreign utility companies for distribution of natural gas. Although heat fusion of polyethylene is a reliable joining process, equipment malfunctions, environmental conditions and deviations from the joining procedure can generate a variety of defects at the fusion interface. Strict quality control of the fusion joining procedure can significantly reduce the likelihood of fabricating a defective joint, but defective joints have been fabricated under ideal environmental conditions without any observable deviation from recommended joining procedures. To assure public safety and avoid the cost of excavating defective butt fusion joints that may develop a leak or catastrophically fail in service, an inspection tool for assessing the structural integrity of butt fused joints has been developed.

Inspection procedures currently practiced by the gas utilities include visual examination of the fusion bead and a variety of ultrasonic testing methods. These procedures involve a subjective interpretation of the results and have been shown to be unable to detect all of the types of critical defects that occur in butt fusion joints. Although an unacceptable visual appearance of the fusion bead is a consistent indicator of a defective fusion joint, a visually acceptable fusion bead does not reliably assure the absence of flaws at the fusion interface. It has been found that degradation of the mechanical integrity of butt fused joints often occurs before a defect is sufficiently large or severe to affect the appearance of the fusion bead. Thus, visual acceptability is a necessary but insufficient condition for assuring a good fusion joint. To supplement visual examination of the fusion bead, some utility companies ultrasonically inspect polyethylene pipe joints using manual contacting techniques. However, because of the nature of flaws in fused polyethylene, manual ultrasonic techniques do not reliably detect all the types of flaws in butt fused joints. The problems with these various manual ultrasonic inspection techniques were not fundamentally intrinsic to ultrasonics technology, but were found to be a matter of inadequacies specifically related to the particular manual techniques that were developed for this application.

For example, the manual ultrasonic inspection procedure of standard practice ASTM F600-78 involves manually moving a transducer around the pipe's circumference and maintaining proper alignment with respect to the weld interface while also attempting to interpret the observed signals on an oscilloscope. One difficulty with this procedure is that the constant attention of an experienced operator is required to simultaneously scan the joint, maintain acoustic coupling between the transducer and pipe, and interpret the signals on an oscilloscope. In addition, interpretation of the inspection results have been found to be very operator dependent, and the reliability of this method is directly dependent upon the skill of the individual operator. The acoustic coupling between the transducer and pipe is inefficient for several reasons which results in a poor signal to noise ratio with only a small portion of the acoustic energy being transferred into the pipe. This reduces the detectability of flaws and increases the chance of incorrect interpretation of the test results. Another problem with this approach is poor transducer design for this application. The curved surface of the pipe causes divergence of the ultrasonic beam, which, unless it is compensated for, results in decreased flaw sensitivity.

Ultrasonic flaw detection depends on the interaction of a propagating elastic stress wave with the discontinuities or gradients in material properties resulting from the presence of a flaw in the material. The wave interaction with a flaw is observed or detected indirectly by the manner in which the flaw perturbs one or more wave propagation parameters. The perturbation of the wave propagation parameters are typically observed as changes in wave speed, propagation direction due to specular or diffuse reflections, and attenuation due to scattering or absorption by the flaw. The material properties effected by the presence of a flaw are generally the density and the elastic moduli, but the specific properties effected depends on the physical nature of the flaw. For example, lack of bond produces a discontinuity in the dynamic tensile and shear moduli at the fusion interface since the unbonded interface cannot support tensile or shear stresses. The magnitude of the effect of these perturbations of the material properties on ultrasonic wave propagation is further influenced by the specific size, shape and orientation of the flaw.

Ultrasonic waves for inspecting pipe joints are usually generated by piezoelectric transducers. For high frequency ultrasonic waves to propagate from the transducer into the pipe wall, the transducer must be acoustically coupled to the pipe. Acoustic coupling of the transducer and pipe can be accomplished by using a variety of solids, fluids and viscous gels depending on the specific constraints of the application. The selection of the coupling medium directly influences the detectability of flaws because the properties of the coupling medium determine boundary conditions governing the wave propagation behavior at the pipe/couplant interface. The important properties of the coupling medium are its wave speed, density and attenuation.

Acoustic coupling between the ultrasonic transducer and the pipe surface is necessary because propagation of ultrasound in air is attenuated too severely for frequencies above 500 kHz and the mechanical impedance mismatch between air and a solid material causes nearly one hundred percent of the ultrasonic energy to be reflected from the surface of the solid material. Thus, almost no ultrasonic energy would be transmitted into the pipe with a concomitant loss of flaw sensitivity. Adequate acoustic coupling generally requires a fluid filled path between the transducer and the test object.

Conventional embodiments of acoustic coupling methods involving a liquid filled path are, in terms generally used by practitioners of ultrasonic testing, water jets, bubblers and immersion. The problems with the first two methods, water jets and bubblers, is that they often generate excessive noise in the ultrasonic signal which diminishes flaw detectability. A specific disadvantage of the water jet coupling method for a portable inspection system is that it requires a large volume of water and precise control of the water flow rate to maintain a hydrodynamically stable column of water.

Immersion which requires a reservoir of water large enough to contain the test object is generally incompatible with the constraints and requirements of field inspection. The system developed and applied in the present invention has combined the benefits and advantages of the small water volume of the bubbler and the absence of noise and efficient acoustic coupling characteristic of the immersion method. The new system involves attaching the scanner assembly to a container which opens in a "clam shell" fashion and when closed surrounds the scanner, transducer and fusion joint. The container is filled with a suitable fluid and emptied automatically during the inspection.

Non-destructive testing by ultrasonic wave propagation techniques in the past are revealed in the following U.S. Pats. Nos.: 4,472,975; 4,084,444; 3,958,451; 3,848,461. In these patents, various means are provided to propagate ultrasonic energy into pipe line materials and monitor signals. The reflected signals are sometimes termed echoes.

U.S. Pat. No. 4,084,444 - Lewis and U.S. Pat. No. 3,848,461 -Hetherington et al. shown apparatus and means for conveying an ultrasonic probe assembly in circular rotation along a steel tube or pipe. A transducer array is revealed to provide signal propagation at various angles to the tubing wall.

U.S. Pat. No. 4,472,975 - Beck et al. discloses an apparatus adapted to closely follow the contour of a pipe while carrying an ultrasonic transducer that is constructed to be angularly adjusted responsive to the selection of precise settings of the transducer holder, and the focal distance for the beam propagated by the transducer. A couplant cavity containing a couplant material is provided between the transducer and the test object.

U.S. Pat. No. 3,958,451 - Richardson discloses an ultrasonic test apparatus for detecting flaws in a weld on steel pipe including a carriage and electronic detection equipment with apparatus to present a graphic electronic representation of the signals returned. Signals returned are recorded by a light beam chart recorder. The recorder wave form is indicative of the characteristic internal structure of the pipe, but no means is provided to objectively evaluate the results nor to discriminate concerning an acceptable number of unobjectionable small "flaws" or irregularities.

The prior art addresses the problems associated with steel and magnetic pipe materials in which differences in the temperature, in the typical environmental temperature ranges at the inspection sites, have negligable effect on the ultrasonic wave propagation in the material.

SUMMARY OF THE INVENTION

An objective of this invention is to provide a method and system for automated ultrasonic inspection of polyethylene butt fusion joints between objects and particularly objects of annular cross section, to accomplish appropriate transducer orientation with respect to various size objects, and to eliminate subjective operator interpretation of raw data from ultrasonically generated electronic signals. Furthermore, improvement of the signal to noise ratio compared to existing practice by the use of a liquid couplant apparatus and appropriate transducer desing is a further objective.

Accordingly, the invention encompasses an ultrasonic apparatus for detecting flaws in an annular test object, comprising a stationary ring for mounting on a test object. The apparatus further comprises a rotating ring mounted via wheels on the stationary ring, for rotation around the test object. A transducer carriage means is provided for removable mounting on the rotating ring, and a motor drive means is mounted on the stationary ring flange for driving the rotating ring by a gear train means. A plurality of ultrasonic transducers are mounted at various angles in transducer blocks mounted on the transducer carriage means.

A source of couplant fluid is provided, and a couplant container means is attached to the rotating ring. The couplant container which is an integral part of the transducer carriage has rubber lip seals for maintaining a fluid tight seal by contacting the test object. The couplant container is an annular cavity machined in the transducer carriage and provides a circular reservoir for containing couplant fluid around the pipe joint. Means for filling the couplant container with the couplant fluid is provided. In addition, means for electronically acquiring and analyzing the flaw data gathered by the ultrasonic transducers, and for visually displaying a predetermined objective indicia of acceptability concerning the integrity of the test object, are provided.

The means for electronically collecting and analyzing the flaw data include a multi-channel pulser through which electronic data is transmitted to a microprocessor, and a liquid crytal display upon which the predetermined indicia of acceptability is visually displayed.

The apparatus may further comprise an adapter mounted between the rotating ring and the test object, which allows for the analysis of various sizes of test objects.

The means for filling the couplant container includes valves for initial filling of the container and for pressure maintenance after the container is filled, so as to minimize noise due to couplant motion during analysis and thereby maximize the signal to noise ratio.

The couplant container means and carriage means are removably mounted so that the apparatus may be applied to the analysis of various sizes of test objects.

The transducers are mounted in the transducer blocks at angles providing for the detection of flaws of sizes with lateral dimensions greater than or equal to 0.031 inches at all depths in the test object.

Typically, three ultrasonic transducers are used for 4-inch pipe, and two ultrasonic transducers are used for 2-inch and 3-inch pipe.

The invention further encompasses in a test apparatus a method for detecting flaws, comprising scanning the test object with a plurality of ultrasonic transducers, which are mounted in a scanning assembly which surrounds the test object. The method further includes electronically collecting and analyzing the flaw data gathered by the ultrasonic transducers, and visually displaying a predetermined objective indicia of acceptability or rejection concerning the integrity of the test object. Most preferably the predetermined indicia of acceptability is a word or phrase, such as "accept" or "reject", visually displayed on a liquid crystal display. Furthermore, the location of flaws detected by each transducer are displayed in a graphic representation of the pipe joint on the liquid crystal display.

According to the method, the ultrasonic transducers rotate about the exterior surface of the test object, and are coupled to the surface via a liquid couplant in which the transducers are immersed, within the scanning assembly.

Also according to the method, the scanning assembly is adjustable for sealingly contacting and scanning the entirety of test objects of varying size.

Finally, the invention encompasses a system for detecting flaws in a test object, comprising means for scanning the test object with a plurality of ultrasonic transducers, which are mounted in a scanning assembly which surrounds the test object. The system further comprises means for electronically collecting and analyzing flaw data gathered by the ultrasonic transducers, and for visually displaying a predetermined conclusive indicia of acceptability concerning the integrity of the test object. Most preferably, the predetermined indicia of acceptability is a word or phrase such as "acceptable" or "rejected", visually displayed on a liquid crystal display. Also displayed are flaw locations and relative magnitudes of flaw signals.

BEST MODE FOR CARRYING OUT THE INVENTION

Figure 1:
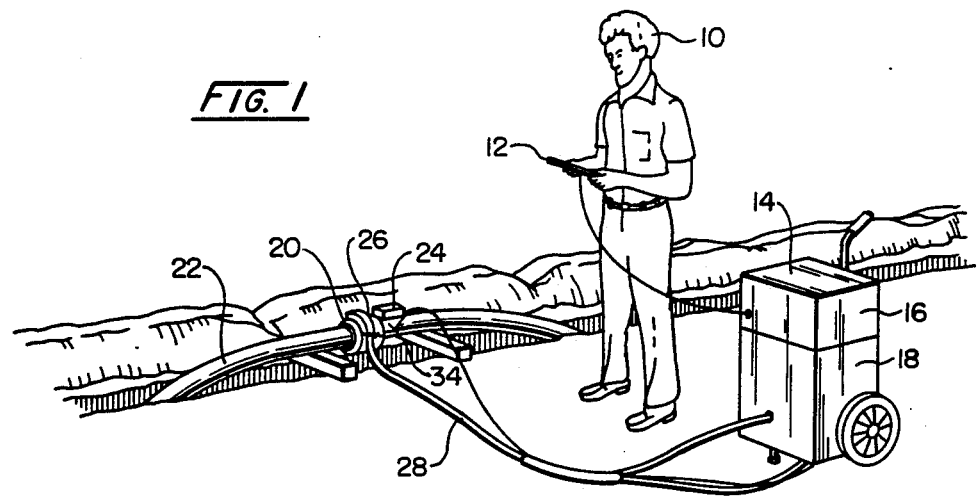
FIG. 1 is a diagram illustrating a field operation of an apparatus of the present invention.

Referring to FIG. 1, basic operation of the invention is illustrated. An operator 10 holds a pendant 12 which includes a liquid crystal display (LCD), or other visual display, upon which the final assessment of pipe joint integrity is shown, and upon which various controls are located. A cart 14 carries a housing 16, for the remaining electronic apparatus, as well as a couplant fluid reservoir 18. A scanning assembly 20 is attached around the pipe 22, and a DC motor means 24 is attached via a bracket 34 to a stationary ring 26 of the scanning assembly 20. A conduit 28 conveys the couplant fluid from the reservoir to a couplant container 46 (see FIG. 2 and 3) of the scannig assembly 20.

Scanning Assembly

Figure 2:
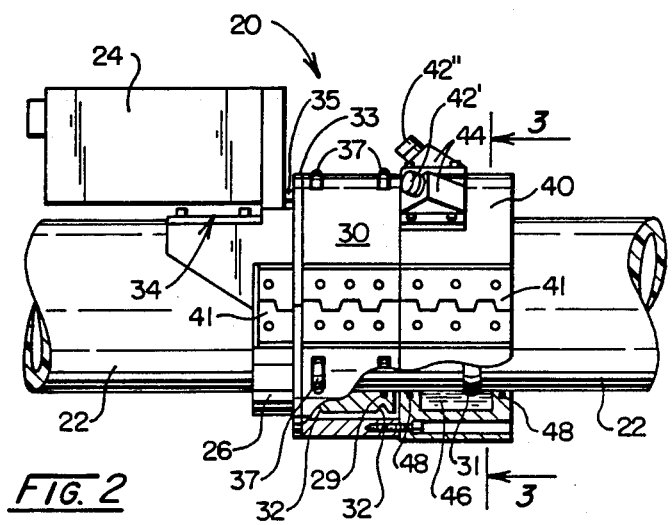
FIG. 2 is a side elevational view of a drive motor and scanning apparatus of the present invention when attached to a large (four inch) diameter pipe.
Figure 4:
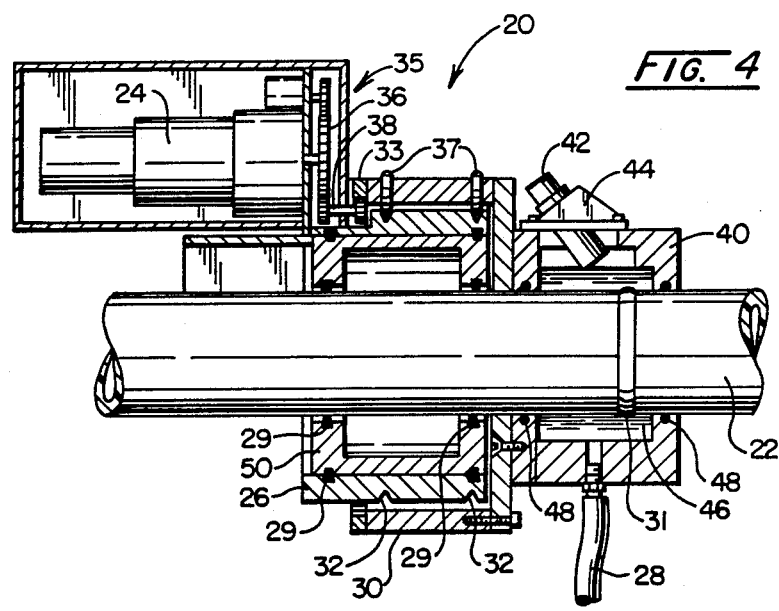
FIG. 4 is a side elevational view of the drive motor and scanning apparatus when attached to a smaller (two inch) diameter pipe.

Referring to FIGS. 2 and 4, the stationary ring 26 is mounted on the annular test object or pipe 22. Mounted on the inside surface of the stationary ring 26 are sectors of extruded rubber which act as a compliant standoff 29 between the stationary ring and the pipe. Since most pipes are slightly oval the compliant rubber standoff serves to center the stationary ring 26 on the pipe 22. The stationary ring 26 is positioned axially along the pipe with respect to the fusion joint or weld bead 31 by using a positioning tool, described below. A rotator ring 30 is rotationally mounted on the stationary ring 26. The stationary ring has two v-grooves 32 which provide a track on which the rotating ring 30 rides via a plurality of wheels 37. A DC drive motor 24 is permanently mounted on the stationary ring 26 by means of a bracket 34. the motor drives a gear assembly 35 including a spur gear 36 and a spool gear 38. Gear assembly 35, in turn drives, a ring gear 33, which is fastened to rotating ring 30 so as to rotate the rotating ring 30 about the stationary ring 26. The wheels 37 are provided in a set of three pairs, spaced 120° apart about the central axis.

FIG. 2 ullustrates the assembly used for a 4-inch pipe, but the same stationary ring 26 and rotating ring assembly 30 are used for a plurality of various pipe sizes including 2-inch, 3-inch, and 4-inch pipe.

A transducer carriage 40 is fixedly mounted on the rotating ring 30 at the side interface between them. Three ultrasonic transducers 42 (see FIG. 3) are mounted in transducer blocks 44 spaced radially 30° apart about the central axis of the carriage 40.

A couplant container receptacle 46 is constructed in the transducer carriage 40. The envelope of container 46 completely surrounds the joint area of the pipe 22 and the weld bead 31. The transducers 42 are immersed in the couplant fluid, preferably water. The edges of the container 46 are provided with rubber lip seals 48 which meet the pipe so as to contain the couplant and so as to compensate for small variations in pipe roundness or relative eccentricity between the two pipe 22 sections that have been joined.

Each carriage 40 with container 46 is specifically sized for the particular pipe size being scanned. Hence, each is removably mounted on the rotating ring 30.

The stationary ring 26, rotating ring 30 and carriage 40 are each split into two 180° sections to allow installation of the scanner assembly 20 on continuous lengths of pipe 22. The three subassemblies are fitted with hinges 41 and over center latches 43 so that they can be easily installed and secured to the pipe 22 for joint inspection.

Figure 3:
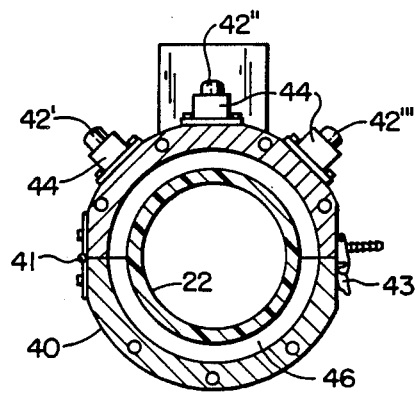
FIG. 3 is an end view of the drive motor and scan apparatus taken along line 3—3, of FIG. 2.

Referring to FIG. 3, the three transducers 42 are mounted approximately 30° apart on one 180° section of the carriage 40.

FIG. 4 illustrates the scanner assembly 20 when attached to a smaller 2-inch pipe. The motor 24 and drive means 35, together with stationary ring 26 may be identical to those illustrated in FIG. 2 for the larger pipe assembly, but the carriage 40 and couplant container 46 are specifically sized to fit the smaller pipe. Furthermore, a spacer ring 50 is fitted and bolted to the inside surface of the stationary ring 26 so as to adapt it to the smaller pipe size. The spacer 50, like the stationary ring 26, is fabricated with extrued rubber standoffs 29 on the inner surface for compliancy with the outer diameter of the pipe.

For smaller 2-inch pipe, only two transducers 42, and hence two blocks 44 are used. The two transducers are mounted approximately 60° apart on one 180° section of the carriage 40.

For other pipe sizes, such as three inch an analogous transducer scanning assembly is used, with the spacer ring 50, carriage 40 and container 46 being sized appropriately for the 3-inch pipe.

Figure 7:
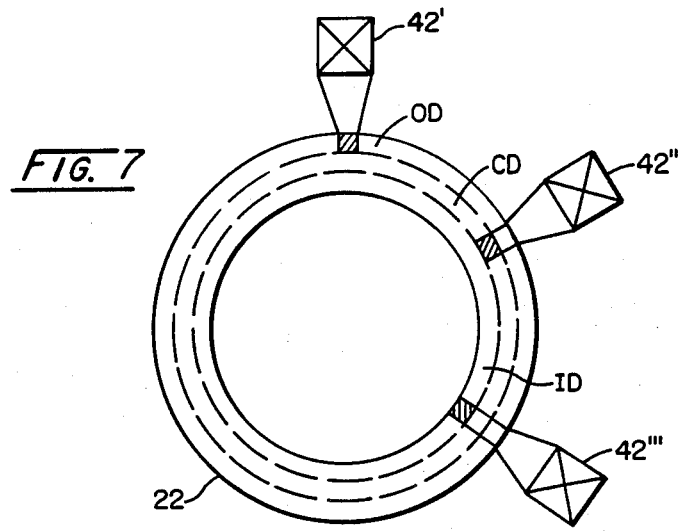
FIG. 7 is a diagram illustrating three transducers of the apparatus when mounted about a larger pipe, showing the zone of the pipe scanned by each transducer.

Referring to FIG. 7, the three transducers 42 for the 4-inch pipe scanning assembly are mounted at varying angles with respect to the longitudinal axis of the pipe 22, so that each focuses on a specific depth in the pipe thickness. The transducer 42' focuses on the outer diameter section OD, the transducer 42" focuses on the center section CD of the pipe, and the transducer 42''' focuses on the inner diameter section ID. The angles to a normal to the pipe surface and the longitudinal axis for the transducers 42', 42", 42"40, have preferably been found to be optimum at 40°, 38°, and 34°, respectively.

In operation, carriage 40 assembly rotates clockwise 360° while the first transducer 42' scands, then rotates counterclockwise 360° while the second transducer 42" scans, and then rotates 360° clockwise again while the third transducer 42"40 scans. The carriage 40 then returns 360° counterclockwise to the starting position. This procedure is used so that the coaxial cable from the multi-channel pulser 66 to transducers 42' 42", 42''' does not become entangled and need not be of excessive length.

In an apparatus and system constructed reducing the invention to practice, cylindrically focused, 2.25 Mhz transducers were used in the preferred embodiment. Each transducer was positioned and oriented to obtain maximum sensitivity at a particular region of the weld bead 31 interface.

Inspection System

Figure 5:
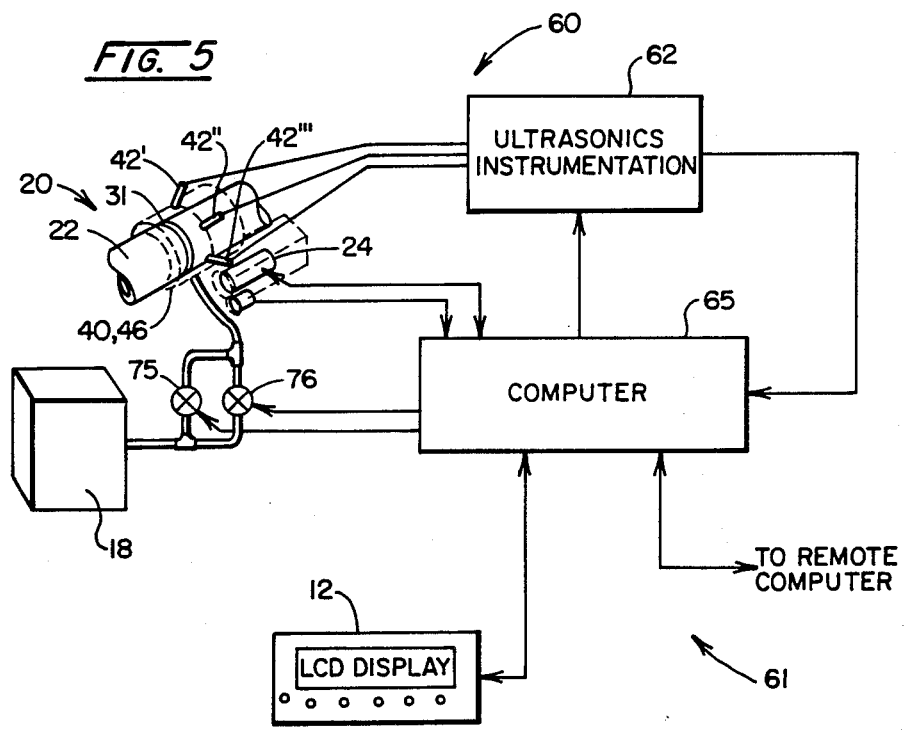
FIG. 5 is a diagram illustrating the function of the electronic or computer control system.

The inspection system, illustrated in FIG. 5, is composed of three sybsystems:(1) an ultrasonics and acoustic coupling subsystem 60, (2) a data acquisition and controls subsystem 61, and (3) mechanical subsystem 20.

The ultrasonics and acoustic coupling subsystem 60 is comprised of the ultrasonics instrumentation 62, transducer array 42', 42", 42''' and hardware components 40, 41, 43, 44, 45, 46 required for containment and distribution of the acoustic coupling. The specific components of ultrasonic instrumentation 62 are a multi-channel pulser, receiver, gate, pulse convertor, transducer array and acoustic couplant container 46 or envelope. The multi-channel pulser operates the appropriate elements in the transducer array; the receiver amplifies a flaw signal; the gate provides a time analog circuit to extract the flaw signal from other irrelevant signals, and the pulse convertor converts the radio frequency (RF) flaw signal within the gate to a direct current (DC) signal of proportionate amplitude.

The data aquisition and controls subsystem 61 includes the computer and associated electronics hardware necessary for automating the operation of the inspection system and performs the data processing to determine the acceptability of the fusion joint. The expertise for inspecting the polyethylene pipe joints resides in a microprocessor/computer 65 which performs or controls the various system operations. The functions of the microprocessor 65 include: (1) controlling the motion of the mechanical scanner assembly 20, (2) selecting the required pulser channels to activate the appropriate transducer array elements for the pipe size at an appropriate time during scanning by the transducer array, (3) adjusting the receiver gain required for the specific transducer array element, pipe size and pipe material, (4) adjusting the delay and width of the time analog gate appropriate for each transducer array element, pipe size and pipe material, (5) storing the digitized output of the pulse convertor, (6) executing commands entered by the operator from the menu driven, liquid crystal graphics display pendant 12, (7) displaying flaw locations and whether to accept or reject the pipe joint, and (8) controlling the couplant flow to the transducer array.

The mechanical subsystem 20 includes the hardware necessary for the automated scanning motion of the transducer array elements around the pipe 22 and for providing the precise orientation and positioning of the transducers necessary for successful field implementation of the ultrasonic test method.

The details for each of these subsystems are presented below.

Figure 8:
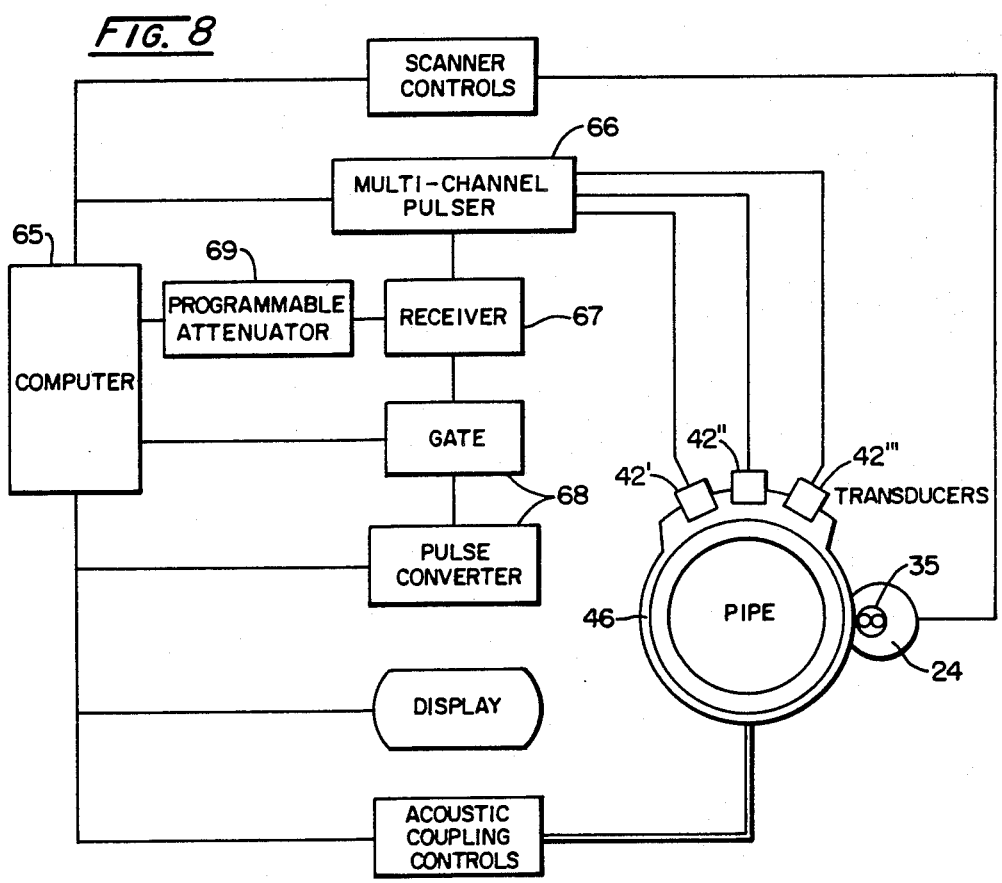
FIG. 8 is a block diagram illustrating the principal components of the ultrasonic inspection system.

Referring to FIG. 8, the ultrasonics instrumentation 60 consists of five basic components which are: the ultrasonic transducers 42', 42", 42''', a multi-channel pulser 66, a receiver 67, a programable attenuator 69, and a gated pulse convertor 68.

In a unit constructed according to the invention, the ultrasonic transducers were electrically connected to the multichannel pulser 66 using coaxial cable. Two types of coaxial cables, 178B/U (MIL-C-17D) and 58C/U (MIL-C-17D), have been used and both were acceptable. The transducers accepted male UHF connectors. To achieve a weather resistant electrical connection between the transducers and coaxial cables, it was necessary to use a UHF to type N adaptor. However, other weather resistant, water proof connector may be available.

The multi-channel pulser was a Model 800, KB-Aerotech instrument manufactured by KrautKramer-Branson,, Inc. which was modified in this invention. The modifications were provided to allow the computer 65 to trigger the pulser 66 and to select the appropriate pulser channel during the transducer scanning sequence. The multi-channel pulser was also repackaged in a single enclosure with the other ultrasonic instrumentation 62.

The receiver was an instrument, Model MR106, manufactured by MetroTek, Inc. The receiver 67 amplifier was set at its maximum gain of 60 decibels (dB). In operation, the receiver amplifies the RF electrical signal produced when an ultrasonic wave is incident on the piezoelectric transducers 42', 42", and 42''''. This amplification is required to increase the RF signal to an acceptable voltage level for the other signal conditioning electronics. Sufficient gain was also required so that the voltage of the RF signal for the minimum flaw size to be detected is larger than the 200 millivolt switching transients present in the time analog gate portion of the gated pulse convertor 68 described below. If the voltage of the flaw signal were smaller than the gate switching transients, then the presence of the flaw signal would not be discernable after digitization even though the flaw signal could be visually observed on an oscilloscope. Another function of the amplifier is to increase the voltage of the RF flaw signal so that the DC output voltage from the pulse convertor 66 was significantly larger than the 20 millivolt resolution of the digitizer, but less than the 5 volt maximum input level.

Because the signal from different transducers in the array may vary greatly, programmable attenuator 69 is used to adjust the signal amplitude so that the signals from the various transducers occur within approximately the same voltage range, and to avoid saturating the digitizer with signals from small flaws or system electrical noise. The attenuator used was Type 50MDA63 manufactured by Alan Industries. It is programmable from zero to sixty three dB in one dB steps. Internally the attenuator has six relays which are transistor buffered from the computer. This gives the computer 65 six control lines to select from zero to sixty three dB of attenuation.

The gated pulse convertor was a Model MD702, instrument manufactured by MetroTek, Inc. This instrument produces a time analog gate that can be turned on and off by the computer and has computer controllable time delay range from 0.2 to 800 microseconds. The pulse convertor 68 output is a DC voltage that is proportional to the peak-to-peak voltage of the gated RF signal. This converted DC signal is digitized by the computer 65 analog-to-digital converter during the scanning process and is stored in memory for subsequent data processing.

As shown in FIGS. 2, 3 and 4, the transducer array conceived and constructed for this invention consists of multiple oriented transducers and provides optimized positioning of the individual transducers with respect to the fusion interface. Multiple transducer orientations have been found to be necessary to detect flaws over the full pipe wall thickness and to achieve adequate probability of detection for different flaw types, sizes and geometries. A separate transducer array is required for each pipe size as shown in FIGS. 3 and 4 to mechanically adapt the inspection system to different pipe diameters. Also, because of the variation in the transducer type and orientation required to inspect the various wall thicknesses for different pipe sizes, various array configurations were provided. In the 4-inch array, three transducers are orineted at nominal angles of 40, 38 and 34 degrees with respect to a normal to the pipe surface longitudinally. These orientations optimize flaw sensitivity to the outer (OD), center and inner (ID) regions of the wall thickness for 4-inch pipe. For 2-inch pipe only the two transducers oriented at 40 and 38 degrees were used. For 2-inch pipe either transducer in the array can detect flaws over most of the pipe wall thickness but the two array elements were used to provide the multiplicity of incident angles important for enhancing flaw detectability. The transducer arrays 42 and carriages 40 are interchanged to adapt the inspection system to the desired pipe size.

An integral part of the transducer array 42 and carriage 40 is the couplant container 46. The container 46 is automatically filled with water from a manually pressured three gallon tank 18 to acoustically couple the transducer and pipe. A semi-watertight seal is maintained between the couplant envelope and the pipe by the two lip seals 48. The lip seals 48 compensate for small variations in pipe roundness and relative eccentricity between the two sections of joined pipe. The carrage 40 with couplant container 46 opens in "clam shell" fashion, in order that the assembly may be easily attached to or removed from the pipe 22. The pressurized couplant tank 18 is constructed as a tank with a built-in, manually operated plunger type pump. Two solenoid valves 75 and 76 in parallel are used to control the water flow rate to the couplant container 46. One valve 75 provides a large volume of water or high flow rate, and the other valve 76 restricts water volume to a low flow rate. To quickly fill the envelope, both solenoid valves are opened automatically at the appropriate time during the inspection cycle. During scanning of the pipe 22 the high flow rate valve 75 is automatically closed and only the low flow rate valve 76 remains open to compensate for the small leakage from the couplant container. Both valves are closed automatically at completion of the inspection cycle.

Since, for this invention, it is necessary to minimize all possible noise sources, the acoustic coupling method described above was conceived and found to be superior to the more conventional water jet, transducer wheel, and bubbler. These conventional coupling methods generate excessive ultrasonic noise for the system of this invention and diminish flaw detectability. Another disadvantage of a water jet for a completely portable inspection system is the large volume of water and precise control of the water flow rate required to maintain a hydrodynamically stable water column.

The data acquisition and controls subsystem 61 (FIG. 5) was conceived to automate all aspects of the ultrasonic inspection process and to require minimal operator training. Ease of use, both in the lab and in the field, along with an architecture sufficiently flexible to accommodate future enhancements are objectives of the invention. An important feature of the inspection system was the development of a user-friendly operator interface including a visual, liquid crystal (LCD), display for executing the system commands necessary to automate the insepction and development of automatic assessment of the quality of butt-fused polyethylene joints. The display is at the surface of the pendant 12.

The controls apparatus includes the drive motor 24 on the scanner mechanism 20, the solenoid valves 75 and 76 connected between the couplant container 46 and the tank 18, the pendant 12 and the remote computer 65.

Referring further to FIG. 5, the central component of the controls apparatus includes the microcomputer 65 which is responsible for selecting and taking data from the ultrasonic transducers 42, controlling the scanner motor 24, regulating the flow of couplant to the container 46, providing information to an operator through the pendant control panel 12 containing the visual or liquid crystal display (LCD), and communicating with a remote central processing unit (CPU) if desired.

The ultrasonic instrumentation generates and conditions the signals from the transducers. The computer controls the triggering of the pulser, selection of the appropriate pulser channel, signal attenuation, and gating of the ultrasonic flaw signal. The conditioned ultrasonic signal is then digitized and stored by the computer during the scanning process for processing to determine the acceptability of the pipe joint.

During rotation about the pipe the speed and position of the mechanism 20 is controlled by the microprocessor 65. During operation, the position of the transducers 42 and carriage 40 is determined by feedback from a potentiometer. As a safety feature a torque feedback circuit is provided, with operation based on monitoring the motor current, and implemented to remove power to the motor should the moving portion of the mechanical assembly 20 become jammed or when a preset torque limit is exceeded.

The pendant 12 control panel provides information to the operator. It displays easy-to-use menus on a flat panel LCD from which the operator can select the task to be performed and the pipe size and material to be inspected. Software defined switches minimize the number of switches needed to operate the system. During the scanning process, the pendant LCD displays the position of the transducers along with the graphic information about the location of flaws in the joint. After scanning has been completed, the computer 65 assesses the quality of the pipe joint and displays a graphic representation of the location of flaws detected by each transducer in the array. Also displayed is the decision to accept or reject the pipe joint.

A serial communication port of a RS-232 type is provided to enable data to be transferred to a second remote computer (not shown) or other digital recording device after a joint has been inspected, should the user decide to maintain a permanent record of pipe joint inspections.

Microprocessor

Figure 10:
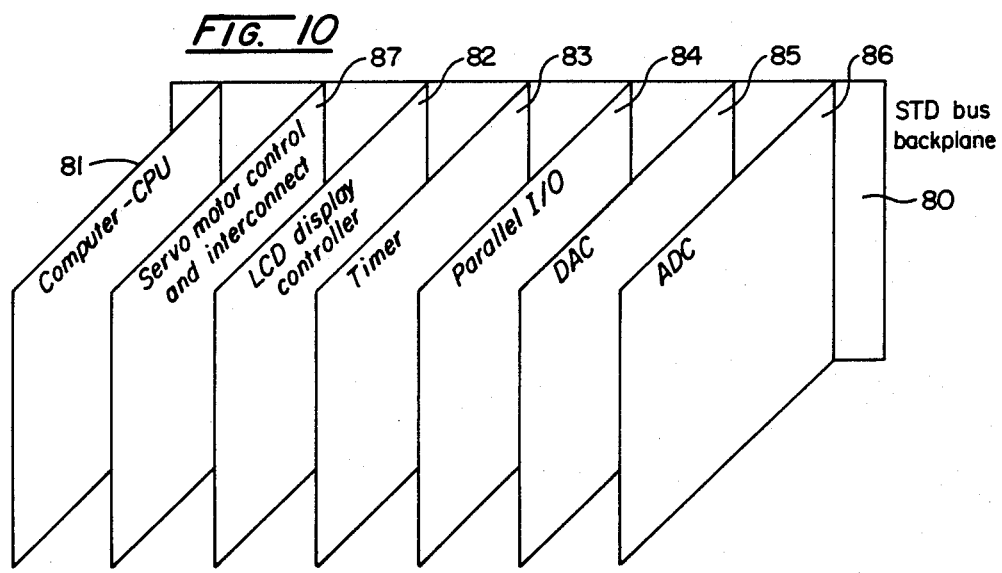
FIG. 10 is a schematic view of the microprocessor and control cards as configured in a standard (STD) bus back of this invention.

The standard (STD) bus back plane 80 and configuration of computer cards are illustrated in FIG. 10. The servo motor controller and interconnect card were not actually a part of the STD bus system, but used the slots in the card cage for power and as a convenient location next to the other cards. The computer 65 was powered by a heavy-duty triple output power supply.

The CPU card 81 was a MCPU-800 manufactured by Miller Technology. This card contains a Z-80 microprocessor, 32K read only memory (ROM), 64K random access memory (RAM), 24 lines of digital input/output (I/O), and a serial port. The MINT-01 is the RS-232 option which is used as a standard communications protocol with other computers. Only five of the 24 digital I/O lines are used for inputs from the pendant function switches. Modifications were made to the CPU card to allow the mode two interrupts to operate.

The display controller card 82 interfaced the flat panel LCD to the STD bus. The LCD used was a Seiko Instruments, Model F2416 display having 240 horizontal pixels by 64 vertical pixels. The display controller was an Hitachi HD61830. This integrated circuit (IC) uses 4K of local RAM to store the pixel data. The computer accesses the RAM indirectly through commands to the display controller IC. Both the graphics and alphanumerics displayed on the LCD were drawn in the graphics mode on a pixel-by-pixel basis.

The timer was a Pro-Log, Model STD 7000 card having three channels of timer/counters. The card was modified to allow it to operate at 10 MHz so that the timers would have a 100 nanosecond resolution.

The timer card 83 generates the trigger for the multichannel pulser and the gate signal for the gated pulse converter module. Channel "zero" operates in the free running mode and is the trigger for the multichannel pulser. Its timing determines the repetition rate for the ultrasonic pulser. Channel "zero" also triggers channel "one" which is configured as a one-shot timer. Channel "one" in turn triggers channel "two", also configured as a one-shot timer. The output of channel "two" is the gate control signal. The gate delay time is thereby determined by the channel "one" time period and the gate width is determined by the channel "two" period. This method of gate control assures accurate timing with minimal CPU interaction.

The parallel input/output (I/O) card 84 is used to control the couplant valves 75 and the attenuator, the scanner motor 24 speed, the transducer 41 selection, the torque limit reset, and the emergency stop inputs. The I/O card is a Mostek Corporation Model MDX-PIO card which uses two Z-80 PIO chips. These PIO chips could be configured for mode two interrupts, however only port A1 is configured in this way. If the preset torque limit for the motor 24 is exceeded or other emergency stop signals become active, the port A1 will generate an interrupt to the CPU. All other ports are configured as control outputs.

The digital-to-analog converter (DAC) 85 is a Data Translation, Model DT2727 card. This card has four channels of analog output, each having 12 bits of resolution and a ±/−5 volt range. The primary purpose of this card is to provide the position command for the servo motor 24. At the moment, the other three channels were not used; however, future system modifications or options could include using the other channels to generate a permanent record of the inspection results on a strip chart recorder or some other recording device.

The analog-to-digital convertor (ADC) 86 was a Matrix Corporation, Model 7911/ADC-12 card. This card has eight channels of multiplexed differential analog inputs, two of which were used. The ADC converts analog inputs ranging from −5 to +5 volts into 12 bit values. Channel "zero" is used to digitize the ultrasonic signals and channel "one" is used to read the position of the carriage 40.

The servo motor controller and the interconnect card 87 was a multi-function board used to hold the low power components of the servo motor controller and receives it power from the STD bus. The board served as a junction point for wiring interconnections between the other computer cards and the device external to the computer. The debounce circuitry for the pendant function switches were also on this board.

The power supply was a Model M281-115, triple output power supply assembly manufactured by Pro-Log Corporation. This supply has a +5 volt output at 10 amps and +12 and −12 volt outputs at 1 amp each. The STD card cage was a Pro-Log Corporation, Model BN12T which provides 12 slots.

Scanner Mechanism Operation

The scanner mechanism is rotated about the pipe by a DC servo motor 24 with speed and position feedback as discussed previously. Since the DC servo motor current is proportional to torque, if the scanner mechanism jams, the electronics can sense the excessively high current and trip a relay to automatically disconnecting power to the motor before the inspection system or the operator is harmed. The details of how this feature is implemented is discussed below and illustrated in FIG. 11.

Figure 11:
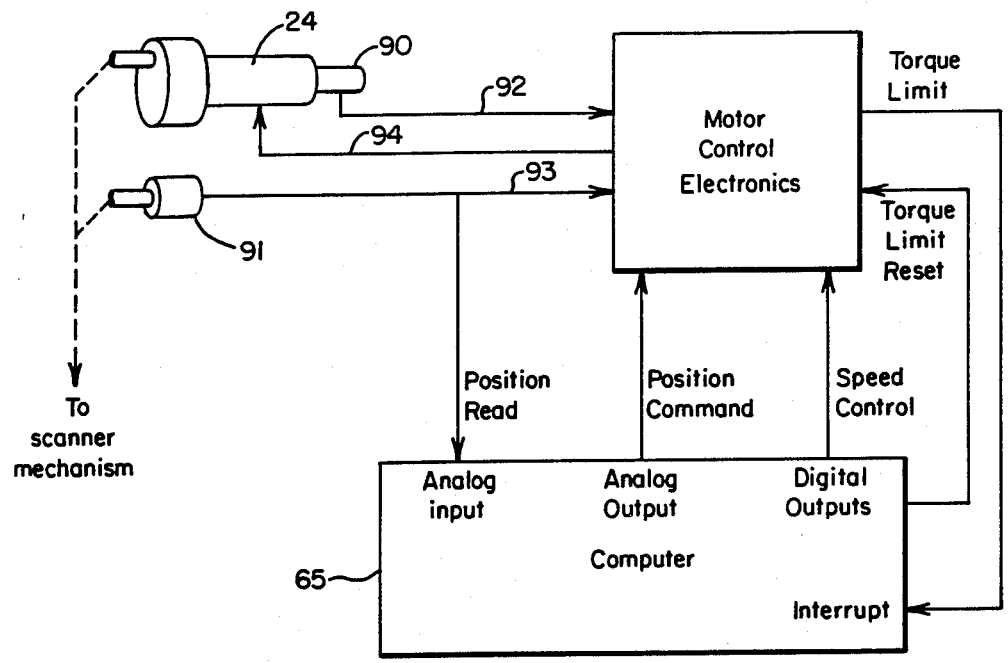
FIG. 11 is a schematic diagram of the speed control and position feedback scanner mechanism of this invention.

The computer controls the servo motor as illustrated in FIG. 11 by issuing a position and speed command.

The position command is an analog signal generated by the computer's DAC card. The DAC's output range is from +5 to −5 volts which corresponds to positions of 380 to −20 degrees of rotation, respectively. Having 12 bits of resolution, the DAC can issue positions to within 1 part in 4096. The speed command is a three bit digital value allowing eight possible speeds to be selected. The position of the scanner mechanism is read by one channel of the ADC. The ADC reads the position with the same resolution with which the DAC issues positions so that the computer stops the motor by reading the position from the ADC and then immediately issuing this same position to the DAC.

The servo motor control electronics consists of amplifiers which use speed and position feedback signals to continually adjust the power input 94 to the motor 24. The circuitry senses three drive mechanism parameters: (1) speed, via a tachometer 90, (2) position, via a potentiometer 91 and (3) torque, via a current shunt. For each of these parameters there is a control signal supplied by the computer or pre-set by a potentiometer.

A principal component of the servo control electronics is the speed error/power amplifier. This amplifier serves the dual purpose of supplying the high currents to drive the motor 24 and regulating the motor speed through the negative feedback input 92. The positive input to the speed error power amplifier is the speed command. The absolute value of the voltage of this input governs the speed while the polarity controls the motor's direction. The speed is selected by an analog switch and a resistor ladder voltage divider. At the lower end of the ladder, the voltage is lower and thus the speed is slower. At the upper end of the ladder, the voltage is higher providing a correspondingly faster speed. The analog switch is used to select the tap along the resistor ladder and thereby adjust the motor speed.

The position of the transducer array is determined by a potenitiometer mounted on the mechanical scanner assembly. The position error amplifier measures the difference in the position command and the actual position. This signal is used as the command for the speed control portion of the servo motor. For large positional differences, the output of the amplifier is clipped to about ±/ −5 volts. This allows the motor to run at a constant speed while moving from one position to another. When the servo motor is close to its commanded position, the error voltage approaches zero thus causing the motor to slow and stop. The gain of both the speed control and position control amplifiers were selected to give rapid, low error responses without oscillations.

Operation and Software Architecture

A primary objective in the invention is to make the system easy to operate. This is accomplished by a software configuration that enables the system control functions and tasks executed by the system to be organized into a set of menu selections.

Upon system power-up or resetting the system, there is an initialization process which sets the default conditions and rotates the scanner mechanism to a home position. Once initialized, the system enters the main menu mode which gives the operator a choice of four operation modes. The four operation modes displayed on the pendant 12 displayed menu are:

1. TEST PIPE - this mode performs the operations necessary for field inspection and assessment of pipe joint quality. 2. MOVE SCANNER - this mode enables the operator to rotate the scanner after acquiring data in the test pipe mode and provides the capability to mark flaw locations on the pipe. 3. CALIBRATE - this mode is to verify the satisfactory performance of the ultrasonic electronics when the system is attached to a calibration standard. 4. MANUAL - this mode was implemented during reduction to practice of the system to access and change the operating parameters.

Inspection Process

Another important aspect of the invention is the automation of the inspection process. The inspection process consists of scanning, data acquisition, data processing, and displaying the results of the processed ultrasonic data. The inspection process can be executed from either the test pipe or the manual operation modes. Upon initiating a scan the computer executes the software commands to move the scanner mechanism to a home position if it is not already in that position. After reaching the home position, data acquisition can be initiated and consists of storing in memory the digitized flaw signal for every degree of rotation. The flaw locations are displayed in a graphic representation of the fusion joint as the data is acquired. After data acquisition is completed, the data is processed and the results are displayed.

The operating parameters required during the inspection process (the attenuator setting, the gate delay time and width, the upper and lower thresholds, and the upper and lower integration rejection levels) are stored in a data base. This information is specific to each combination of transducer array elements, pipe size, and pipe material. Therefore, the data base is a three dimensional array having seven elements per array index.

Data Base

The data base is a structure in the C programming language. The structure is called "config" and is organized as shown below.

| config [xducer] [pipesize] [material] | |
|---|---|
| int atten, | (attenuation setting) |
| int delay, | (gate delay time) |
| int width, | (gate width) |
| int lthres, | (lower threshold setting) |
| int uthres, | (upper threshold setting) |
| int linteg, | (lower integration rejection level) |
| int uinteg, | (upper integration rejection level) |

Each element of the structure is a 16-bit integer. The "xducer" index variable ranges from zero to five which corresponds to possible transducer array elements one through six, respectively. However, only three of the six available transducer channels have been utilized. The index variable "pipesize" ranges from zero through four corresponding to 2-inch, 3-inch, 4-inch, 6-inch, and 8-inch pipe diameters. The material index variable can take the values of zero, one, or two which corresponds to TR-418, M-8000, and ALDYL-A polyethylene pipe materials, respectively. The data base is, thus a six by five by three array of seven, 16-bit values occupying 1,260 bytes of memory.

During the scanning procedure, the motor is activated and data is taken from the ultrasonics instrumentation. The scanner overscans the inspection area by starting five degrees before the zero or home position and scans past the ending point by five degrees. This assures that the entire area of the pipe is inspected.

The scanning process is started when the computer issues the ending position to the servo motor. Once the appropriate command is executed, the servo motor rotates the scanner mechanism at a constant speed around the pipe. Data is taken and stored in memory for every degree of rotation. While the scanner is rotating, the computer reads the position and waits until the scanner reaches the next degree increment. When the next position is reached the computer digitizes the ultrasonic signal and saves the data in memory. This continues until the entire circumference of the pipe has been inspected.

The liquid crystal display is controlled by a large scale integrated circuit which accepts command and display parameters from the computer. The software configures the format of the display and writes the pixel data to the display RAM in the computer. The display interface routines are written in Z-80 assembly code so that the display can be updated quickly.

A function called D.INIT initializes the display to operate in the graphics mode. The display screen is organized as 240 horizontal pixels by 64 vertical pixels. The X-Y coordinate system has its origin at the upper left-hand corner of the screen. The X direction range is zero through 239 and the Y direction range is zero through 63.

In most display systems, the hardware converts the ASCII information stored in the display memory into the character fonts seen on the screen. However, because the LCD operates in an entirely graphics mode, the characters are software generated by drawing the pixels which make up the fonts. The routine which converts ASCII data into a character on the display is called D.ISOUT. The character fonts occupy 5 horizontal by 7 vertical pixels; blank rows along the top and bottom and a blank column along the right-hand side of the character font are added. The blank rows put a border around the characters so that inverted text is completely highlighted.

Text can be positioned anywhere on the LCD display by the D.CURSOR routine. The X and Y coordinates passed to this routine are the upper left-hand corner position of the first character of the text to be generated. A blank column of nine vertical pixels is placed along the left of the first character so that inverted text will have inverted pixels along all sides.

Routines were also written to clear the display, set and clear individual pixels, and set the screen base. The routine D.CLRSCN will clear the entire screen. D.CLEAR will clear a specified number of lines starting at a given Y location. To turn on a pixel at a given X-Y location, D.SETDOT will do this without affecting any neighboring pixels. D.CLRDOT will turn off a pixel at the specified X-Y location. D.BASE is the routine which sets the starting memory location or the base of the screen.

Pendant Control Panel

There is enough memory on the pendant LCD control panel 12 to hold two entire screens at once. Even though the LCD controller can not display two overlapping screens, it can switch back and forth between the two screens. This is done by changing the memory location from which the controller begins taking display data. The first screen is used to display the main scanner functions while the second screen is used for the emergency stop message. Because the emergency stop interrupts the system, this method was the fastest and simplest way to save the screen at the start of the interrupt routine and to restore the screen just prior to returning from the interrupt routine. Without the second screen, the computer would have to move the data to and from the display memory and the system memory. This would be a more time consuming and complicated procedure.

After data acquisition, the computer must process the data to assess the quality of the joint and tell the operator to either accept or reject the pipe joint. The computer makes this decision based on two integrations of the ultrasonic data around the pipe circumference for each transducer array element. The first integration is performed on the data occurring between a lower and upper threshold and the second integration is performed only on the data occurring above the upper threshold. This gives an upper and lower integration value for each transducer in the array. the upper and lower integration values are compared to the upper and lower integration rejection values stored in the data base. If the upper or lower integration values exceed their respective rejection values the pipe joint is rejected. An upper and lower integration rejection value resides in the data for each possible transducer array element, pipe size and pipe material combination Integration is perfomed by summing the data within the area delimited by the upper and lower thresholds. For each data point, if the data is above the lower threshold and below the upper threshold, then the data value minus the lower threshold level is added to the lower integration sum. If the data is above the upper threshold, then the data value minus the upper threshold level is added to the upper integration sum and the difference between the upper and lower threshold levels is added to the lower integration sum.

This method of processing the ultrasonic data was conceived to avoid rejecting pipe joints containing small, single isolated flaws and at the same time avoid accepting pipe joints with a large population of small flaws. This approach also provides an acceptance decision base on the overall quality of the pipe joint. For example, a single small void at the center of the pipe wall does not measurably diminish the impact strength of a fusion joint. However, large numbers of small voids distributed around the pipe circumference could significantly degrade the mechanical strength of the joint. Implementation of the fusion quality assessment criteria described above enables the inspection system to discriminate between these two cases. Thus, a single small void can be accepted by the inspection system but a pipe joint containing many small voids will be rejected.

Since the integration thresholds and rejection values can be different for each transducer, pipe size and pipe material the acceptance criteria for flaws near the outer and inner surfaces of the pipe can be made more restrictive. This is advantageous because flaws in those locations are more likely to initiate pipe joint failures. Also, if it is known that a particular pipe material exhibits a lower fracture toughness than another material, then the acceptance criteria can be made to be automatically more restrictive for the inferior material.

Inspection Procedure

The procedure for field inspection of butt-fused joints consists of attaching the appropriate transducer 42 array for the pipe size to be inspected, to the transducer carriage 40, attaching the mechanical assembly to the pipe 22 at the welded bead joint 31, and entering the 37 TEST PIPE" operation mode.

Figure 9:
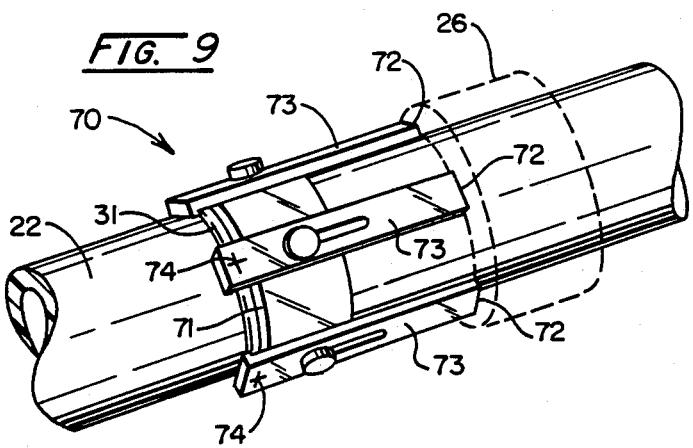
FIG. 9 is a diagram showing a positioning tool means for axially positioning the stationary ring along the pipe with respect to the fusion joint or weld bead.

Referring to FIG. 9, the apparatus 20 is positioned on the pipe using a positioning tool 70. The positioning tool 70 is placed adjacent to the fusion bead 31 at one side 71, and the stationary track ring 26 is butted against the edge 72 of the positioning tool 70. This assures that, when the transducers 42 in the transducer array are attached to the track assembly 26, the array transducers are properly located with respect to the weld 31 interface. The positioning of the transducer array at the proper distance is important for achieving reliable inspection results. The positioning tool 70 compensates for variations in bead width by adjusting three individual gauges 73 on the positioning tool 70 so that a cross-hair 74 is aligned with the fusion bead 31 interface. The distance from the cross-hair 74 to the edge 72 of each gauge on the positioning tool is precisely where the edge of the track assembly should be located in order for the transducer array to be at the proper distance from the fusion interface when attached to the track.

Figure 6:
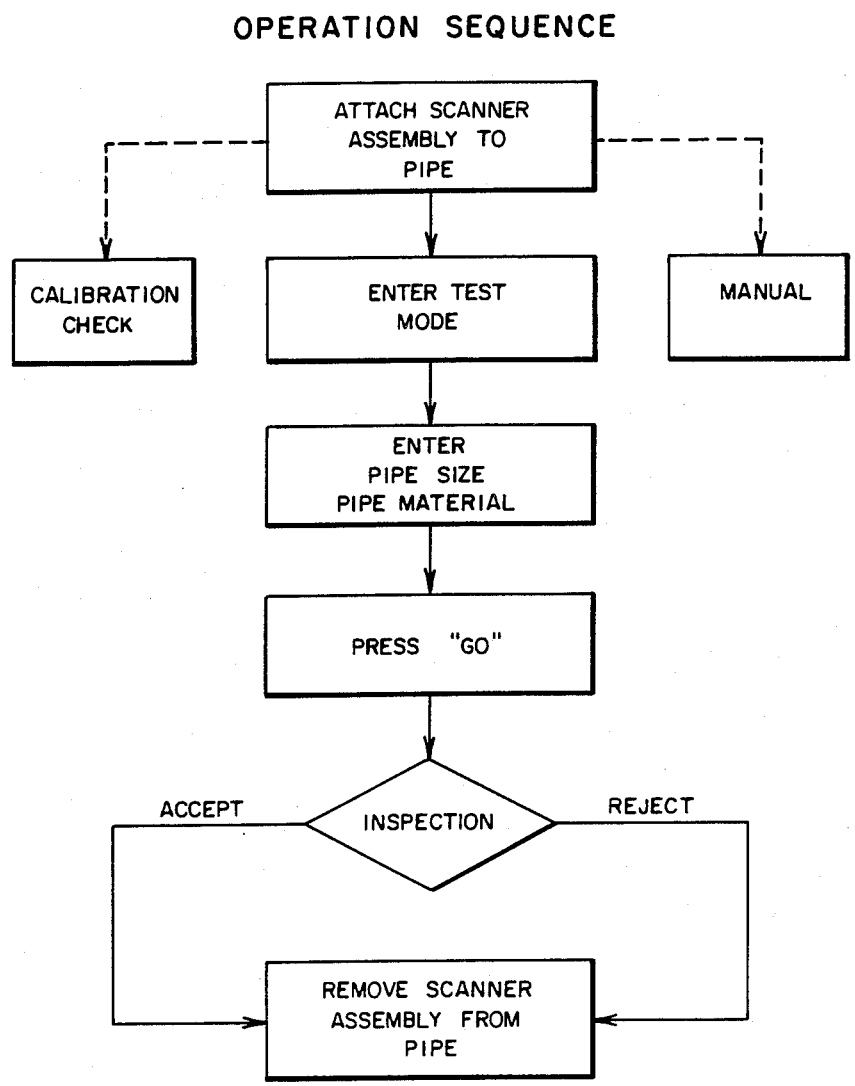
FIG. 6 is a diagram illustrating operational procedures for using the invention.

Referring to FIG. 6, the inspection of a 4-inch pipe joint, including attaching and removing the mechanical assembly 20, requires less than five minutes. Upon entering the "TEST PIPE" mode of operation, the operator is directed to select the pipe size and material to be inspected by indicia on the screen of the pendant 12. This is done using the pendant control panel containing the LCD and software defined function switches. The operator then initiates the inspection process by pressing the function switch beneath the displayed indicium "GO". Upon completion of data aquisition, the microprocessor processes the data to assess the quality of the joint, and the location of the flaws in the pipe joint are displayed on the control panel LCD. Above the graphics display of the flaw locations, the result of the assessment of the fusion joint quality is indicated by the message "ACCEPT PIPE JOINT" or "REJECT PIPE JOINT" as appropriate.

As previously described operation modes are displayed on the pendant control panel 12. The function of each switch is displayed in reverse video (white on black) directly above the switch. Menu selections are made by pressing the appropriate function switch to move a cursor from one selection to the next. The cursor location is indicated by displaying the menu selection at the cursor location in reverse video.

Entering the "TEST PIPE" mode the system executes the sequence of commands and operations. The operator is directed to select the pipe material and pipe size to be inspected. In the example construction, the pipe materials from which a selection could be made included ALDYL-A, TR-418, and M-8000 polyethylene. The pipe sizes that would be selected included 2-, 3-, and 4-inch diameter pipe, although up to 8- inch diameter pipe could appear on the display.

After the pipe size and pipe material are entered, the computer displays a graphic representation of the pipe cross-section and directs the operator to "PRESS GO WHEN READY." During this time, the high flow rate and low flow rate solenoid valves 75, 76 are opened to quickly fill the couplant envelope with water. When the "GO" switch is pressed, the high flow rate valve 75 is automatically closed and the inspection of the pipe joint is initiated. The scanner mechanism 20 makes one revolution around the pipe for each transducer until the entire area of the fusion joint is inspected. After scanning and data acquisition are completed, the low flow rate solenoid valve 76, which has remained opened during scanning to compensate for leakage, is closed. The data is then processed and the results are displayed. The locations of the flaws detected by each transducer in the array are displayed and if the joint is defective the message "REJECT PIPE JOINT" is displayed. If the pipe joint is acceptable the message "ACCEPT PIPE JOINT" is displayed.

The "MOVE SCANNER" mode allows the operator to rotate the scanner mechanism 20 so that flaw locations can be marked on the pipe for destructive evaluation. In this mode, a graphic representation of the cross section of the fusion joint is displayed. The top of the displayed cross section corresponds to the outer surface of the pipe and a cursor at the top of the display denotes the circumferential location of the transducer. The amplitude of the flaw signal at the location indicated by the cursor for the selected transducer is displayed in the upper right-hand corner of the screen. To view information about any one of the transducer channels, the up or down arrow switch is pressed. A marker at the left of the screen indicates which transducer is selected. For 4-inch pipe there are three transducers in the array; one array element to inspect the outer region of the pipe, a second element to inspect the center region, and a third element to inspect the inner region of the butt-fused pipe joint. Thus, if the transducer marker is at the top edge of the displayed cross section the information on the LCD is for the array element that inspects the outer region of the pipe wall. Similarly, if the marker is at the center or lower edge of the displayed cross section, the information is for the central and inner array elements, respectively. To move the scanner the switch under the arrow pointing either to the left or right is pressed. While the switch is depressed the scanner begins to rotate; slowly at first then accelerating to maximum speed.

Temperature Compensation

An important aspect of field inspection of polyethylene butt fusion joints is the effect of temperature on ultrasonic wave propagation in the pipe. This is not a significant problem when inspecting metal pipe, and represents and important distinction between the ultrasonic inspection systems for plastic and metal pipes. Wave speed and absorption of an ultrasonic wave are both functions of temperature of the material in which the wave is propagating. The temperature dependence of ultrasonic wave speed or velocity affects the system performance because velocity changes, in either the couplant or the pipe, changes the refracted angle of the transmitted ultrasonic wave.

Changes in pipe temperature are accommodated by providing a transducer array with a sufficient number of transducer orientations to provide reliable flaw detection over the operating temperature ranges. When the pipe temperature changes sufficiently for a particular transducer to be ineffective for detecting flaws then the ineffective transducer is switched off and a transducer at the appropriate orientation is switched on.

Figure 12:
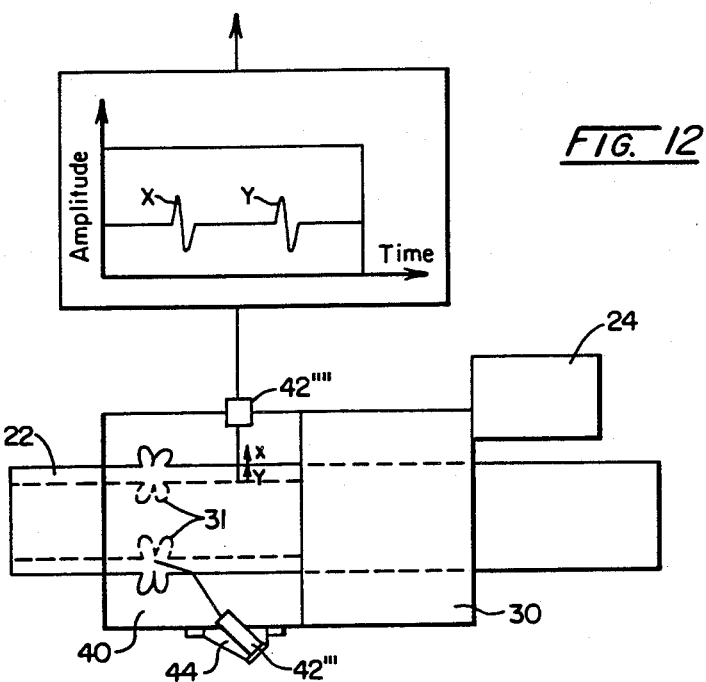
FIG. 12 is a schematic view of the temperature compensation subsystem of this invention.

Referring to FIG. 12, the pipe temperature at which it becomes necessary to switch from one transducer orientation to another is determined by measuring the velocity of a p-wave using a transducer array element $42''\Delta$ oriented perpendicular to the pipe surface. As stated above, it is the velocity temperature dependence that affects the ultrasonic test results and the performance of the inspection system. Therefore, it is specifically the velocity change and not the change in temperature that must be determined; and by measuring the time between reflections X and Y, the ultrasonic velocity in the pipe can be measured automatically. Because the operator has already selected the pipe size as explained previously and illustrated in the operation sequence depicted in FIG. 6, the pipe wall thickness and hence the distances traveled by reflections X and Y are known. By dividing the difference of time-of-flight between X and Y, [X−Y], by the pipe wall thickness, Tw, the velocity, V, is obtained (i.e. V=[X−Y]Tw. In this invention the velocity is measured and the computer determines which array elements should be used to inspect the pipe joint and, thus, automatically compensates for the range of pipe temperatures that can be expected in the field environment.

Figure 13:
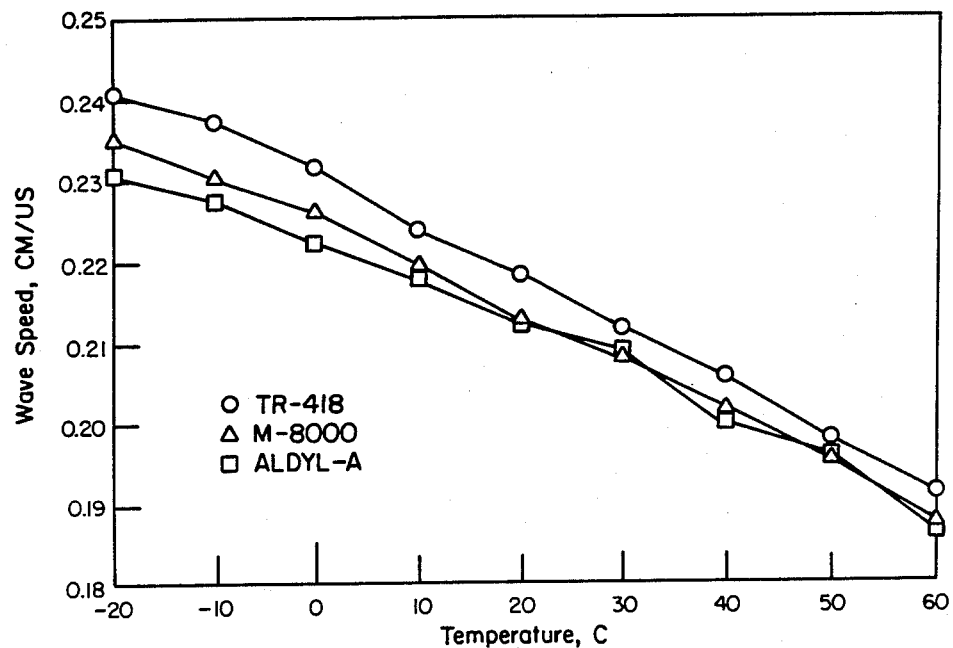
FIG. 13 is data showing the temperature dependence of ultrasonic velocity for three commonly used pipe materials including TR-418, M-8000, and ALDYL-A.

To elucidate the physical principles of compensating for temperature that allow switching transducer arrays on or off, consider the previously described three element array for 4-inch diameter pipe. A fourth transducer element, denoted by 42'''' in FIG. 12, discussed previously in this section, but is mounted in the couplant envelope 40 along with the other three array elements and measures the velocity of an ultrasonic wave in the pipe. The velocity in plastic pipe increases with decreasing temperature as shown in FIG. 13 for three commercial grades of polyeythlene pipe materials: TR-418, M-8000, and ALDYL-A. (Therefore, according to Snell's Law, the angle of refraction (the entry angle of the ultrasonic wave into the pipe) changes.

Figure 14:
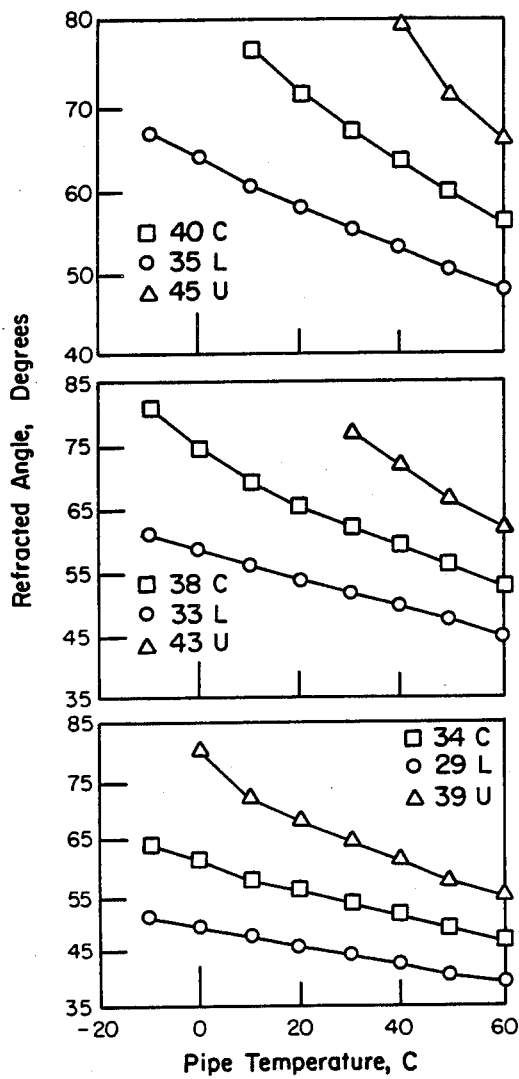
FIG. 14 is plots of retracted angles versus temperature for TR-418 with a water couplant use a velocity for water of $V_w = 1.48$ centimeter per microsecond.

In FIG. 14 the resulting refracted angles measured with respect to a normal vector to the pipe surface is shown for each array element for 4-inch, TR-418 pipe as function of temperature. Because the directivity associated with the emitted waves from an ultrasonic transducer is divergent, the wave is incident over a range of angles at the pipe surface. In FIG. 14 a five degree divergence has been used in the refracted angle calculations. The central angle of the incident diverging wave is denoted by "C" and the upper and lower bounds of the incidence angle are denoted by "U" and "L", respectively. As seen in FIG. 14, as the temperature decreases, the refracted angles for the central, upper and lower bounds of the ultrasonic wave increase and the width of the ultrasonic beam in the pipe increases. Therefore, as the temperature of the pipe decreases there exists a transition temperature at which the refracted angles are too large for a particular array element to inspect the fusion zone and excessive noise or signals from structural features of the fusion joints such as the fusion bead would give incorrect indications of defects in the fusion joint.

Figure 15A:
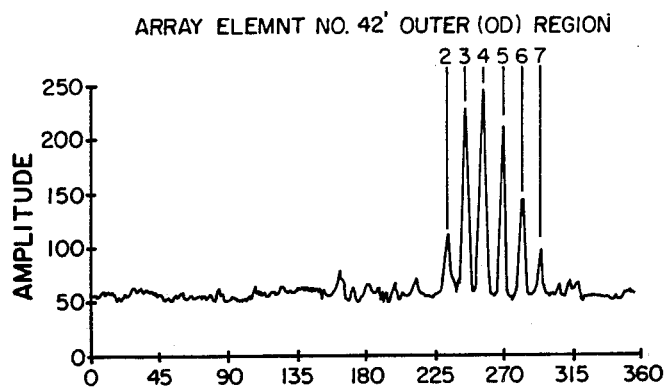
FIG. 15 a, b, c, are data for the three transducer array elements using a pipe joint sample at room temperature containing 10 defects.
Figure 15B:
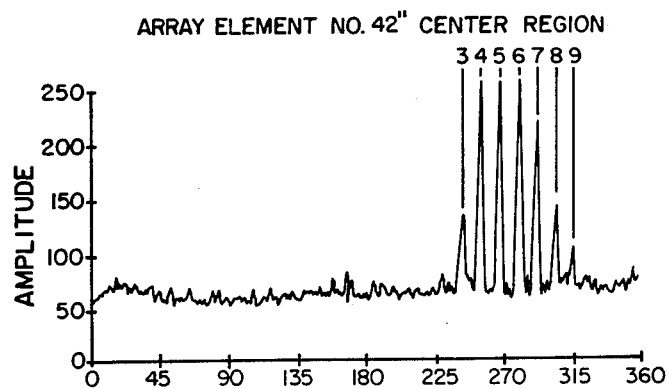
Figure 15C:
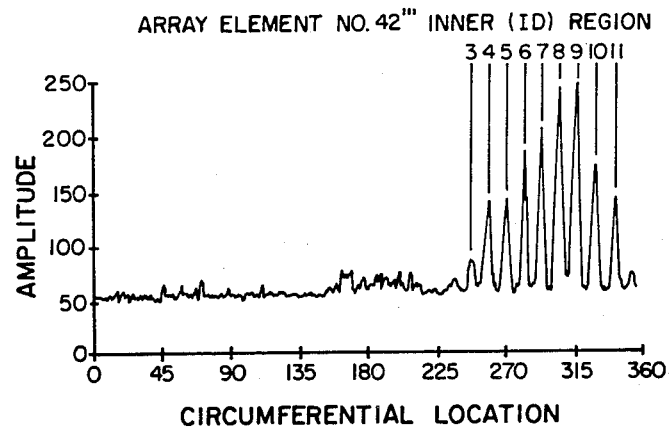
Figure 16A:
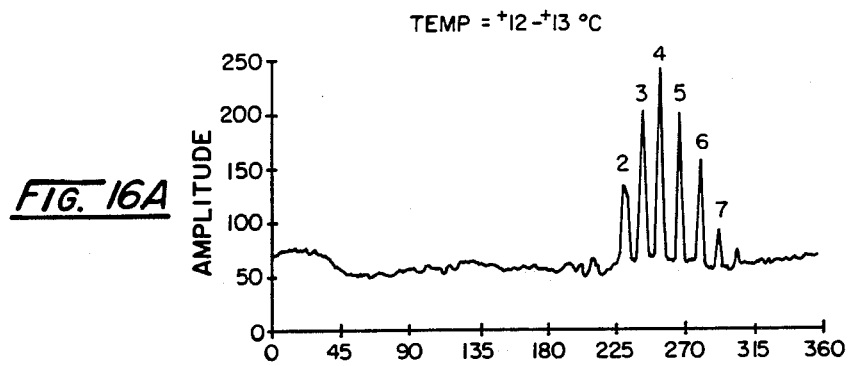
FIG. 16 a, b, c are the data for the sample and array element No. 1 at various temperatures.
Figure 16B:
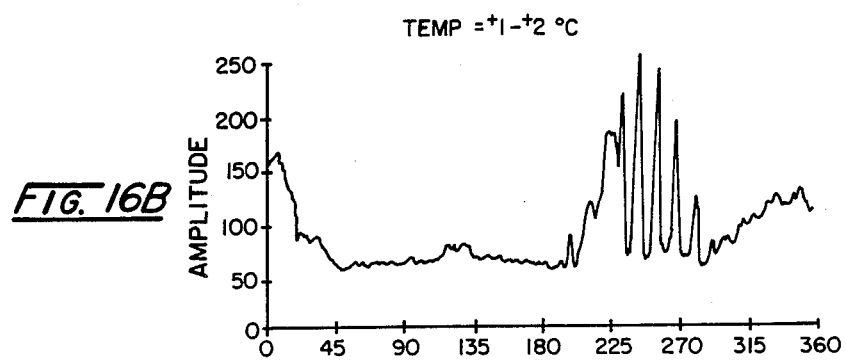
Figure 16C:
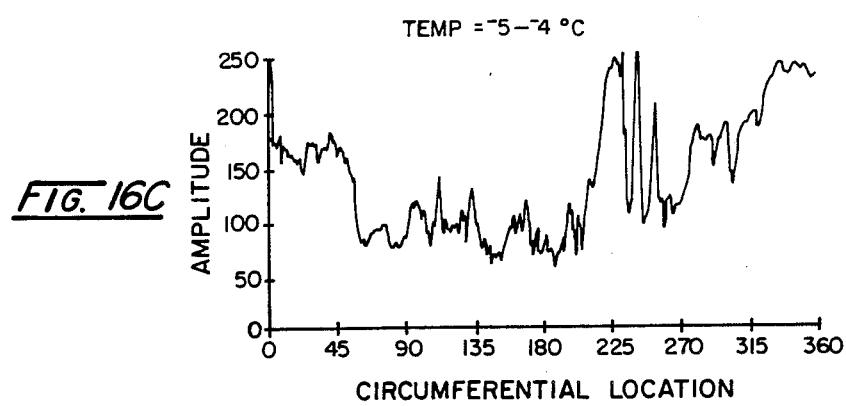

Another effect of decreasing temperature is that attenuation of the ultrasonic wave in the pipe decreases. Based on the experimental results given in FIGS. 15 and 16 a decrease in pipe temperature can be compensated for in 4-inch pipe in the following manner. In FIGS. 15 and 16 circular flaws with 0.031-inch diameters and denoted by the numbers 2 through 11 are distributed around the pipe circumference at the fusion interface from the outer (OD) surface, at flaw number 2, to the inner (ID) surface, at flaw number 11, at incremental depths of approximately 1 mm. The flaw signals obtained for each array element for pipe at room temperature illustrating the sensitivity to flaws across the entire fusion zone are shown in FIG. 15. FIG. 16 shows the signals for a typical array element at lower pipe temperatures. As temperature decreases from about 60° C. to 12° C., the transducer 42' oriented at 40° must be inactivated, and the inspection is performed with the 38° and 34° transducers 42'' and 46'' array elements. Because of the increased refracted angle, increased beam spread, and decreased attenuation in the pipe at the lower temperatures, the 38° and 34° transducers provide over the entire fusion interface sensitivity. As the temperature decreases further from, about 12° C. to 1° C., then the transducer oriented at 38° must be inactivated and the inspection of the fusion joint in 4-inch pipe at temperatures below 1° C. are performed with the single 34° transducer array element. Additional elements to provide smaller incidence angles, say 30° and 26°can be added to the transducer array should it be anticipated that the device will be used at temperatures below 1° C. These array elements would be activated for temperatures below 1° C. to provide the multiplicity of incidence angles at various depths in the fusion zone, as discussed in a previous section of this invention disclosure, to improve the probability of detection of large flaws. The transducer array elements are activated and inactivated automatically by the inspection system central processing unit based on the measured velocity of the ultrasonic wave in the pipe.

Another inspection parameter for which temperature compensation is necessary is the gate delay and width. This is accomplished automatically by enabling the the computer to make the appropriate adjustments based on the velocity measurement described above. The amplifier gain or the pipe joint rejection criteria can be automatically adjusted in the same manner to compensate for temperature if necessary.

It is herein understood that although the present invention has been specifically disclosed with the preferred embodiment and examples, modification and variation of the concepts herein disclosed may be resorted to by the skilled in the art. Such modifications and variations are considered to be within the scope of the invention and the appended claims.

We claim:

1. A method for detecting flaws in an annular test object, comprising:
   a. in a scanning mode, sequentially scanning the test object with a plurality of ultrasonic transducers, one at a time, the transducers being mounted in a scanning assembly that surrounds the test object,
   b. in a readout mode, electronically collecting and analyzing flaw data gathered by said ultrasonic transducers, and visually displaying a pre-determined objective indicia of acceptability or rejection concerning the structural integrity of the test object,
   c. wherein, in the scanning mode, the test object has an annular cross section and the ultrasonic transducers rotate circumferentially about the exterior surface of the test object, and are coupled to the surface via a liquid couplant in which the transducers are immersed within the scanning assembly without requiring immersion of the entire test object, and
   d. wherein, in the scanning mode, each of the ultrasonic transducers is in an array of transducers that is circumferentially rotated 360° about the exterior surface of the test object, with one transducer in a transmission active mode, and with the other transducers in a transmission inactive mode.

2. A method according to claim 1, wherein the liquid couplant is supplied rapidly in a first filling step and slowly in a second leakage compensation step during circumferential rotation of the transducers in the scanning mode.

3. The method according to claim 1, wherein the transducers are rotatable to the position of an unacceptable flaw after a display of predetermined objective indicia of a lack of acceptability.

4. A method according to claim 1, wherein step (b) includes collecting flaw data gathered by the ultrasonic transducers in analog form, digitizing the data, committing the data to memory of a microprocessor, and comparing the data with previously stored data of acceptability to determine and display objective indicia of positive acceptability on non-acceptability concerning the structural integrity of the test object.

5. An ultrasonic apparatus for detecting flaws in a test object of tubular shape and annular cross section, comprising:
   (a.) a stationary mounting ring constructed for fixed clamp mounting on the external peripheral surface of the test object,
   (b.) a rotational ring mounted on the stationary ring, for reversible rotation about the test object, at the clamped position of the stationary ring on the test object,
   (c.) a carriage having a couplant container therein, attached to the rotational ring, supporting at least one ultrasonic transducer, at an angle to the longitudinal axis of the tubular test object,
   (d.) a motor mounted on the stationary ring, driving the rotational ring in rotation on the test object,
   (e.) a source of couplant fluid,
   (f.) the couplant container surrounding the periphery of the object, mounted in said transducer supporting carriage on said rotational ring, and with rubber lip seals for sealingly contacting the test object, the couplant being in ultrasonic coupling contact with the at least one transducer and the test object,
   (g.) means for filling the couplant container with the couplant fluid and
   (h.) means for electronically collecting, storing, and analyzing flaw data gathered by said ultrasonic at least one transducer, and for producing a predetermined objective indicia of acceptability or rejection concerning the structural integrity of the test object.

6. An ultrasonic apparatus as in claim 5, further comprising an adapter mounted between the rotating ring and the test object to adapt the apparatus to fit on and test objects of different sizes.

7. An ultrasonic apparatus as in claim 6, wherein said couplant container and said carriage are removably mounted.

8. An ultrasonic apparatus as in claim 5, wherein the means for filling the couplant container include a rapid flow valve for initial filling of the container and a slower flow valve for maintaining sufficient couplant by compensating for leakage after the container is filled.

9. An ultrasonic apparatus as in claim 5, wherein said means for electronically collecting and analyzing the flaw data include a multi-channel pulser and programmable time analog gate through which electronic flaw data is transmitted to a microprocessor, and a liquid crystal display upon which the predetermined indicia of acceptability is visually displayed.

10. An ultrasonic apparatus as in claim 5, wherein said couplant container and said carriage are removably mounted.

11. A system for detecting flaws in a test object, comprising:
   (a.) means for scanning the test object with a plurality of ultrasonic wave generating transducers, which are mounted in a scanning assembly that surrounds the test object,
   (b.) means for electronically collecting, storing, and analyzing flaw data gathered by said ultrasonic transducers, and visually displaying a predetermined objective indicia of acceptability or rejection concerning the integrity of the test object,
   (c.) means for sensing the speed of the wave generated by the ultrasonic transducer in the material in the object and converting the sensed speed to an electrical signal proportional to such speed, and
   (d.) means for transmitting the electrical signal to the electronic collecting means causing said electronic means to selectively deactivate or activate at least one transducer in the system, when the temperature is below or above a selected amount, respectively, whereby distortion in the output of the scanning and collecting means is reduced when the angle of refraction, velocity, and attenuation of the ultrasonic wave in the material changes because of temperature changes in the material.

12. A system as in claim 11, wherein the predetermined indicia of acceptability is a word or phrase visually displayed on a liquid crystal display.

13. A system according to claim 11 where additional means is provided to transmit the electrical speed responsive signal to the electronic means to adjust the predetermination of the objective indicia.

14. A system according to claim 11 where additional means is provided to transmit the electrical speed responsive signal to electronic means to adjust the operating parameters including gate delay, gate width, and receiver gain to obtain the correct objective indicia.

15. A system for detecting flaws in a test object constructed of a selected material, comprising:
   (a) means for scanning the test object with energy from a plurality of ultrasonic transducers, which are mounted in a scanning assembly that surrounds the test object,
   (b) electronic means for collecting, storing, and analyzing the flaw data gathered by the transducers,
   (c) means for sensing the speed of the ultrasonic wave in the material in the object, and converting the sensed speed to an electrical signal proportional to such speed, and
   (d) means for providing the electrical signal to the electronic means causing the electronic means to selectively deactine or activate at least one transducer in the system, when the temperature is below or above a selected amount, respectively, whereby distortion in the output of the scanning and collecting mean is eliminated when the angle of refraction, velocity and attenuation of the ultrasonic wave in the material changes because of temperature changes in the material.

16. A method for detecting flaws in an annular test object constructed of a selected material comprising:
   (a.) attaching a rotatable annular scanning assembly having a plurality of ultrasonic transducers to the periphery of the test object,
   (b.) operatively connecting the scanning assembly to electronic computer controlled flaw data collecting and analyzing apparatus,
   (c.) initiating the collecting and analyzing apparatus in the test mode,
   (d.) entering an indication of the size and material of the object into the controller of the computer,
   (e.) initiating the operation of the collecting and analyzing apparatus to rotate the scanning assembly 360° around the test object with one transducer scanning while the others are shut off as the assembly rotates 360° and then rotating the assembly an opposite direction with a different transducer scanning while the other transducers are shut off, and continuing to reverse direction in that manner until the scanning transducers have all individually scanned the test object and collecting and analyzing flaw data from the test object, (f.) initiating a visual display indication the flaw data has been analyzed and computed as accepted or rejected, and (g.) detaching the scanning assembly from the object.

17. a method according to claim 16 wherein step (a) includes filling a couplet container surounding the annulus of the object between the periphery of the object and the transducers with a couplant fluid.

* * * * *